US008006535B2

(12) United States Patent
Righini et al.

(10) Patent No.: US 8,006,535 B2
(45) Date of Patent: Aug. 30, 2011

(54) EXPANDABLE PROSTHETIC VALVE CRIMPING DEVICE

(75) Inventors: Giovanni Righini, Chivasso (IT);
Giovanni Bergamasco, Turin (IT);
Gaetano Burriesci, London (GB)

(73) Assignee: Sorin Biomedica Cardio S.r.l., Saluggia (Vercelli) (IT)

( * ) Notice: Subject to any disclaimer, the term of this patent is extended or adjusted under 35 U.S.C. 154(b) by 681 days.

(21) Appl. No.: 11/776,695

(22) Filed: Jul. 12, 2007

(65) Prior Publication Data
US 2009/0018570 A1 Jan. 15, 2009

(51) Int. Cl.
*B21D 41/00* (2006.01)
*B23P 19/04* (2006.01)
(52) U.S. Cl. ............... 72/402; 29/219; 29/238
(58) Field of Classification Search ............... 72/370.12, 72/402, 413, 446, 448, 481.1; 623/62.11, 623/901; 425/392; 29/219, 237, 238, 243.55, 29/244, 280
See application file for complete search history.

(56) References Cited

U.S. PATENT DOCUMENTS

| | | | |
|---|---|---|---|
| 3,363,442 A * | 1/1968 | Kennedy et al. ............... 72/123 |
| 5,042,161 A | 8/1991 | Hodge |
| 5,360,014 A | 11/1994 | Sauter et al. |
| 5,489,296 A | 2/1996 | Love et al. |
| 5,522,884 A | 6/1996 | Wright |
| 5,560,487 A | 10/1996 | Starr |
| 5,669,919 A | 9/1997 | Sanders et al. |
| 5,672,169 A | 9/1997 | Verbeek |
| 5,693,066 A | 12/1997 | Rupp et al. |
| 5,698,307 A | 12/1997 | Levy |
| 5,776,187 A | 7/1998 | Krueger et al. |
| 5,800,531 A | 9/1998 | Cosgrove et al. |
| 5,810,873 A | 9/1998 | Morales |
| 5,814,096 A | 9/1998 | Lam et al. |
| 5,885,228 A | 3/1999 | Rosenman et al. |
| 5,947,993 A | 9/1999 | Morales |
| 5,951,540 A | 9/1999 | Verbeek |
| 5,972,016 A | 10/1999 | Morales |
| 6,019,739 A | 2/2000 | Rhee et al. |
| 6,024,737 A | 2/2000 | Morales |
| 6,051,002 A | 4/2000 | Morales |
| 6,063,102 A | 5/2000 | Morales |

(Continued)

FOREIGN PATENT DOCUMENTS

DE 29911694 8/1999
(Continued)

OTHER PUBLICATIONS

European Search Report issued in EP 07106697, mailed Aug. 21, 2007, 6 pages.

(Continued)

*Primary Examiner* — Teresa Ekiert
(74) *Attorney, Agent, or Firm* — Faegre & Benson LLP

(57) ABSTRACT

A device for crimping an implantable device or a part thereof between a radially expanded condition and a radially contracted condition, includes first and second annular bodies arranged about a common axis, and a ring-like array of linear crimping elements having respective opposite ends linked to the first and second annular bodies, respectively. These annular bodies are relatively rotatable around the common axis between a first position, wherein the annular array of crimping elements define a wider orifice for receiving a device to be crimped, and a second position, wherein the annular array of crimping elements define a narrower orifice.

10 Claims, 6 Drawing Sheets

U.S. PATENT DOCUMENTS

| | | | |
|---|---|---|---|
| 6,110,200 A | 8/2000 | Hinnenkamp | |
| 6,202,272 B1 | 3/2001 | Jackson | |
| 6,277,110 B1 | 8/2001 | Morales | |
| 6,309,383 B1 | 10/2001 | Campbell et al. | |
| 6,350,281 B1 | 2/2002 | Rhee | |
| 6,352,547 B1 | 3/2002 | Brown et al. | |
| 6,387,117 B1 | 5/2002 | Arnold, Jr. et al. | |
| 6,402,780 B2 | 6/2002 | Williamson, IV et al. | |
| 6,454,799 B1 | 9/2002 | Schreck | |
| 6,481,262 B2 | 11/2002 | Ching et al. | |
| 6,506,201 B2 | 1/2003 | DiCaprio et al. | |
| 6,510,722 B1 | 1/2003 | Ching et al. | |
| 6,598,307 B2 | 7/2003 | Love et al. | |
| 6,629,350 B2 | 10/2003 | Motsenbocker | |
| 6,678,962 B1 | 1/2004 | Love et al. | |
| 6,726,713 B2 | 4/2004 | Schaldach et al. | |
| 6,730,118 B2 | 5/2004 | Spenser et al. | |
| 6,769,161 B2 * | 8/2004 | Brown et al. | 72/402 |
| 6,846,324 B2 | 1/2005 | Stobie | |
| 6,915,560 B2 | 7/2005 | Austin | |
| 6,966,924 B2 | 11/2005 | Holmberg | |
| 6,968,607 B2 | 11/2005 | Motsenbocker | |
| 6,981,982 B2 | 1/2006 | Armstrong et al. | |
| 6,988,881 B2 | 1/2006 | Motsenbocker et al. | |
| 7,007,396 B2 | 3/2006 | Rudko et al. | |
| 7,021,114 B2 * | 4/2006 | Perreault | 72/402 |
| 7,069,794 B2 | 7/2006 | Motsenbocker et al. | |
| 7,258,698 B2 | 8/2007 | Lemmon | |
| 7,338,484 B2 | 3/2008 | Schoon et al. | |
| 7,357,814 B2 | 4/2008 | Gabbay | |
| 7,367,984 B2 | 5/2008 | Kulcinski et al. | |
| 7,427,291 B2 | 9/2008 | Liddicoat et al. | |
| 2001/0049558 A1 | 12/2001 | Liddicoat et al. | |
| 2002/0035390 A1 | 3/2002 | Schaldach et al. | |
| 2002/0042651 A1 | 4/2002 | Liddicoat et al. | |
| 2002/0129820 A1 | 9/2002 | Ryan et al. | |
| 2002/0198594 A1 | 12/2002 | Schreck | |
| 2003/0114913 A1 | 6/2003 | Spenser et al. | |
| 2003/0125805 A1 | 7/2003 | Johnson et al. | |
| 2003/0192134 A1 | 10/2003 | Desenne et al. | |
| 2003/0192164 A1 | 10/2003 | Austin | |
| 2004/0039436 A1 | 2/2004 | Spenser et al. | |
| 2004/0123437 A1 | 7/2004 | Kokish | |
| 2004/0193259 A1 | 9/2004 | Gabbay | |
| 2004/0225356 A1 | 11/2004 | Frater | |
| 2005/0166389 A1 | 8/2005 | Perreault et al. | |
| 2005/0197695 A1 | 9/2005 | Stacchino et al. | |
| 2005/0197696 A1 | 9/2005 | Duran | |
| 2005/0229670 A1 | 10/2005 | Perreault | |
| 2005/0234537 A1 | 10/2005 | Edin | |
| 2005/0240256 A1 | 10/2005 | Austin | |
| 2005/0267529 A1 | 12/2005 | Crockett et al. | |
| 2005/0283232 A1 | 12/2005 | Gabbay | |
| 2006/0004469 A1 | 1/2006 | Sokel | |
| 2006/0074486 A1 | 4/2006 | Liddicoat et al. | |
| 2006/0178470 A1 | 8/2006 | Stacchino et al. | |
| 2006/0265855 A1 | 11/2006 | Stenzel | |
| 2007/0027534 A1 | 2/2007 | Bergheim et al. | |
| 2007/0056346 A1 | 3/2007 | Spenser et al. | |
| 2007/0061009 A1 | 3/2007 | Spenser et al. | |
| 2007/0100356 A1 | 5/2007 | Lucatero et al. | |
| 2007/0162113 A1 | 7/2007 | Sharkawy et al. | |
| 2007/0173861 A1 | 7/2007 | Strommer et al. | |
| 2008/0262603 A1 | 10/2008 | Giaquinta et al. | |
| 2009/0192603 A1 | 7/2009 | Ryan | |
| 2010/0249661 A1 | 9/2010 | Righini et al. | |
| 2010/0262043 A1 | 10/2010 | Sauter et al. | |

FOREIGN PATENT DOCUMENTS

| | | |
|---|---|---|
| DE | 102004019254 | 7/2005 |
| EP | 401199 | 1/1995 |
| EP | 515324 | 12/1996 |
| EP | 0778009 | 6/1997 |
| EP | 1174098 | 1/2002 |
| EP | 1353420 | 10/2003 |
| EP | 1690515 | 8/2006 |
| GB | 2083362 | 3/1982 |
| JP | 11332997 | 12/1999 |
| WO | WO 96/39942 | 12/1996 |
| WO | WO 97/24989 | 7/1997 |
| WO | WO 98/14138 | 4/1998 |
| WO | 9953864 | 10/1999 |
| WO | 9953866 | 10/1999 |
| WO | 9955255 | 11/1999 |
| WO | 0006052 | 2/2000 |
| WO | 0021464 | 4/2000 |
| WO | 0030565 | 6/2000 |
| WO | 0119768 | 3/2001 |
| WO | 0121076 | 3/2001 |
| WO | 0121097 | 3/2001 |
| WO | 0121103 | 3/2001 |
| WO | 0121110 | 3/2001 |
| WO | WO 01/76510 | 1/2002 |
| WO | 0211646 | 2/2002 |
| WO | 02092257 | 11/2002 |
| WO | 2006007401 | 6/2005 |
| WO | 2005082578 | 9/2005 |
| WO | 2006088712 | 8/2006 |
| WO | 2006117016 | 11/2006 |
| WO | 2006127089 | 11/2006 |
| WO | 2006136930 | 12/2006 |
| WO | 2007030825 | 3/2007 |
| WO | WO 2008/089365 | 7/2008 |

OTHER PUBLICATIONS

Extended European Search Report issued in EP 07112385, mailed Apr. 1, 2008, 11 pages.

European Seach Report from application No. 07112385.5, mailed Jan. 4, 2008, 6 pp.

Partial European Search Report issued in EP 07112385, mailed Jan. 4, 2008, 5 pages.

Search Report from European Patent Application 07106697.1, dated Aug. 8, 2007.

EP Communication issued in EP 07112385 on Jul. 30, 2009.

International Search Report and Written Opinion issued in PCT/US2010/028873, dated Jun. 15, 2010, 11 pages.

Extended European Search Report issued in EP 10168449, dated Aug. 19, 2010, 3 pages.

\* cited by examiner

Fig_1

EXPANDABLE PROSTHETIC VALVE CRIMPING DEVICE

TECHNICAL FIELD

The present invention relates to crimping devices for use with implantable devices, such as prosthetic heart valves.

BACKGROUND

A wide variety of crimping devices have been developed for crimping stents (e.g., angioplasty stents) onto or within their associated delivery catheters. The term "crimping" is currently used to denote the action of radially contracting an implantable device or a part thereof. A stent for implantation in a body vessel often includes an apertured tubular body that is generally elongated in shape. In other words, the axial length of the stent is larger than, and usually a multiple of, the radial dimension, both in the radially unexpanded and the radially expanded condition of the stent. Many crimping devices known in the art rely on the elongated shape of the stent for proper operation.

Often implantable devices must be crimped to be coupled to implements or tools for conveying the device to the implantation site. The crimping action may involve the entire implantable device or only a portion thereof having an annular shape of reduced length (e.g., an axial length that is smaller than a diameter in an expanded condition). Crimping devices known in the art are not ideal for crimping "short" implantable devices, which do not have an axial length much greater than a diameter. These devices may slide or kink sideways with respect to the plane where the crimping action occurs. Likewise, these devices may become unevenly deformed during crimping and thus may be off-center with respect to the desired crimping axis.

Figure 1:
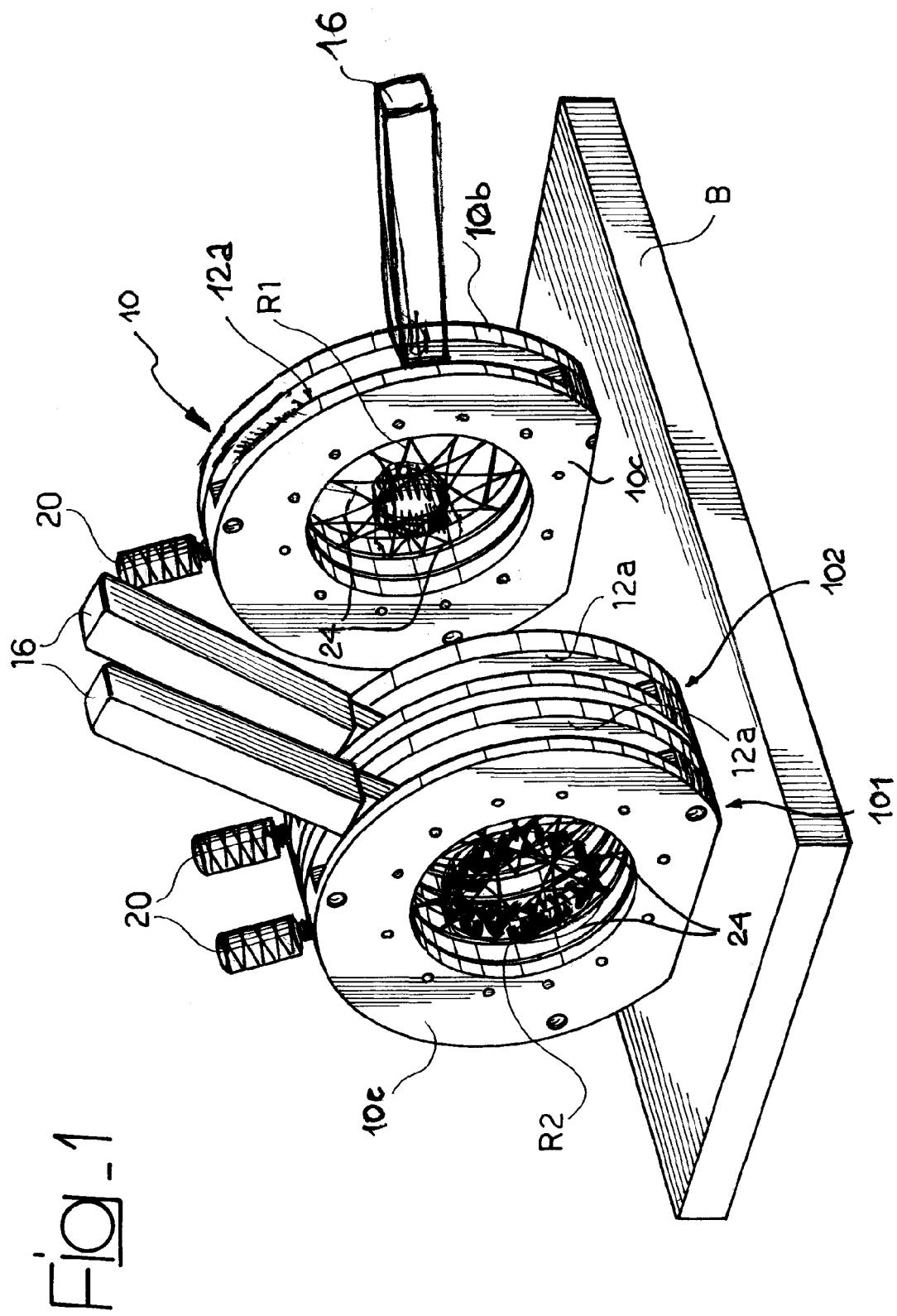
FIG. 1 is a general perspective view of a crimping device as described herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a crimping device adapted for use in crimping implantable devices such as, for example, prosthetic heart valves for minimally-invasive (e.g., "sutureless") or percutaneous implantation, according to one embodiment of the present invention. One such exemplary device is disclosed in EP-A-1 690 515, which is incorporated herein by reference. Such a prosthetic heart valve includes an armature with two annular end sections. These annular end sections are "short" elements, having an axial length that is smaller and generally several times smaller than a diameter in the expanded configuration. In some embodiments, the axial length is a sub-multiple (e.g., ⅕) of the diameter in the expanded configuration. Other exemplary expandable prosthetic heart valves are shown and described in U.S. Publication 2006/0178740 and U.S. Publication 2005/0197695, both of which are incorporated herein by reference.

The device illustrated in FIG. 1 is a multiple crimping tool including a first crimping device 10 adapted for crimping for example, the "inflow" annular end portion R1 of a valve as described in EP-1 690 515, and two "twin" crimping devices 101, 102 adapted for crimping (possibly simultaneously) for example, the "outflow" annular end portion R2 of the same valve. For ease of illustration, FIG. 1 shows only the end portions R1 and R2 of the valve in question.

Arranging two units 101, 102 side-by-side for crimping the outflow portion R2 of the valve may be advantageous. In valves such as those disclosed in EP-A-1 690 515, for example, the inflow portion R1 of the valve carries a tubular pericardium structure comprising the prosthetic leaflets of the valve. This structure provides a certain axial stability to the inflow portion R1 of the valve during crimping. Conversely, the outflow portion R2 is comprised essentially of only the valve armature, so thus may benefit from a crimping action somewhat distributed over its length. Each of the devices 10, 101, and 102 is mounted (e.g., using screws, not visible in the drawing) on a solid base B. The devices 10, 101, 102, the base B, and any related component are comprised of a material suitable for medical use (e.g., polysulfone or Delrin™) and adapted to be easily sterilized.

As shown in FIG. 1, the three devices 10, 101, and 102 are substantially identical. Thus, while the description that follows specifically refer to the device 10, it should be understood that this description also applies to the devices 101 and 102. The device shown in FIG. 1 may be used during an implantation procedure (i.e., in the operational theatre) to crimp, for example, a prosthetic valve just extracted from its sterile delivery package onto the tool or implement (e.g., a catheter) used for implanting the valve into a patient's body.

According to various embodiments, the device or part subject to crimping is self-expandable. Such a device or part may be constructed of, for example, a superelastic material (e.g., Nitinol), which is crimped from a radially-expanded, "relaxed" condition towards a radially-contracted, "constrained" condition against the elastic force of the device or part. According to other embodiments, the device or part subject to crimping is constructed from a plastically deformable material (e.g., stainless steel), which is plastically deformed from a radially-expanded condition towards a radially-contracted condition, for example, for crimping onto an expandable member such as an inflatable balloon located at or near a distal end of an insertion catheter.

Figure 2:
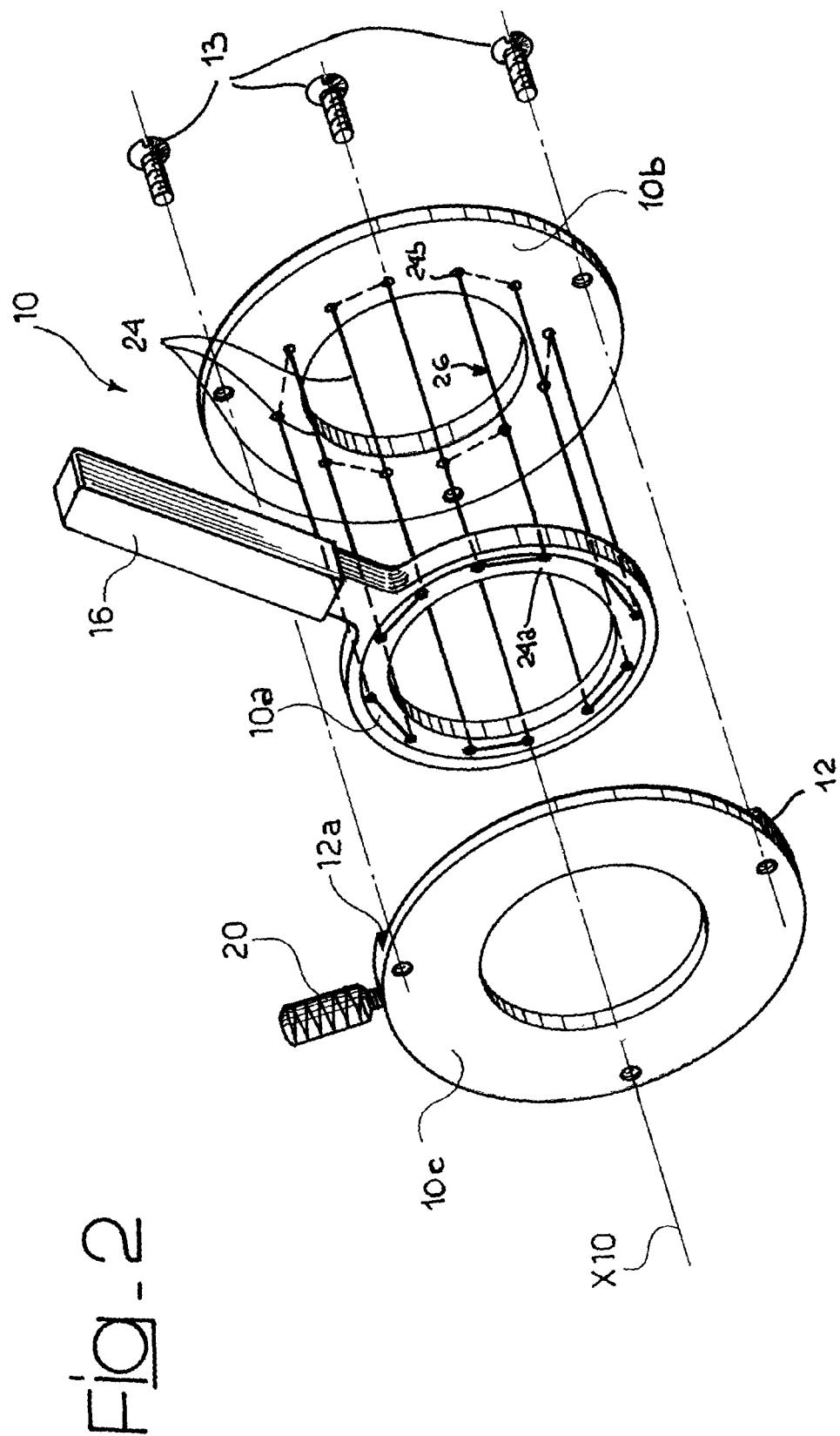
FIG. 2 is an exploded view showing the basic elements of a device as described herein.

As shown in the exploded view of FIG. 2, each of the devices 10, 101, 102 (hereinafter "the device 10") includes two annular bodies 10a, 10b arranged for relative rotation about a common axis X10. A third annular body 10c includes an integral outer circular rim 12 adapted to abut against the outer periphery of the body 10b when the two bodies 10b, 10c are connected to each other via screws 13, with the body 10a interposed therebetween.

The "axial" length (i.e., the length in the direction of the axis X10) and the inner diameter of the rim 12 are selected relative to the thickness and outer diameter of the body 10a in order to ensure radial and axial containment of the body 10a between the two bodies 10b and 10c, while allowing relative rotation of the two bodies 10a, 10b about the axis X10. This relative rotation can be produced by moving a radial arm 16 connected to the body 10a and extending through a slit 12a provided over a given angular length of the rim 12. Either or both of the bodies 10b and 10c are fixed to the base B. Consequently, the arm 16 can be used as an actuating lever to controllably rotate the body 10a with respect to the body 10b.

A screw member or brake member 20 inserted into a threaded radial hole in the rim 12 selectively acts as a brake to fix the body 10a at a given position with respect to the body 10b. Specifically, the brake member 20 is adapted to be loosened and thus radially displaced away from the body 10a to permit free rotation of the body 10a with respect to the bodies 10b and 10c. Conversely, when tightened into the threaded opening, the member 20 advances towards the body 10a to engage the outer periphery thereof and thus prevent rotation of the body 10a around the axis X10.

A screw 13 may be used to couple the bodies 10b and 10c to each other. By removing the screws 13, the body 10a can thus be accessed to remove and replace a linear, wire-like element 26 (e.g., a wire, a suture, a string, a tether, etc.) extending between the bodies 10a and 10b. The wire-like element 26 may include a plurality of crimping elements 24, generally in the form of wire-like formations. The crimping elements 24 are interposed between the two bodies 10a and 10b with each element 24 having a first portion 24a coupled or linked to the body 10a and a second portion 24b linked to the body 10b. As used herein, "linked" is intended to encompass, in addition to a fixed connection, any form of looser association causing the ends 24a, 24b of the elements 24 to follow the respective body 10a, 10b in the relative rotation movement about the axis X10.

In various exemplary embodiments, the body 10b maintains a fixed position with respect to the base B, while the body 10a is selectively and controllably rotated (clockwise, in the example shown) by acting on the "lever" 16. Thus, the ends 24b of the elements 24 will generally retain a fixed or substantially fixed position while the ends 24a will follow the rotation of the body 10a.

Figure 3:
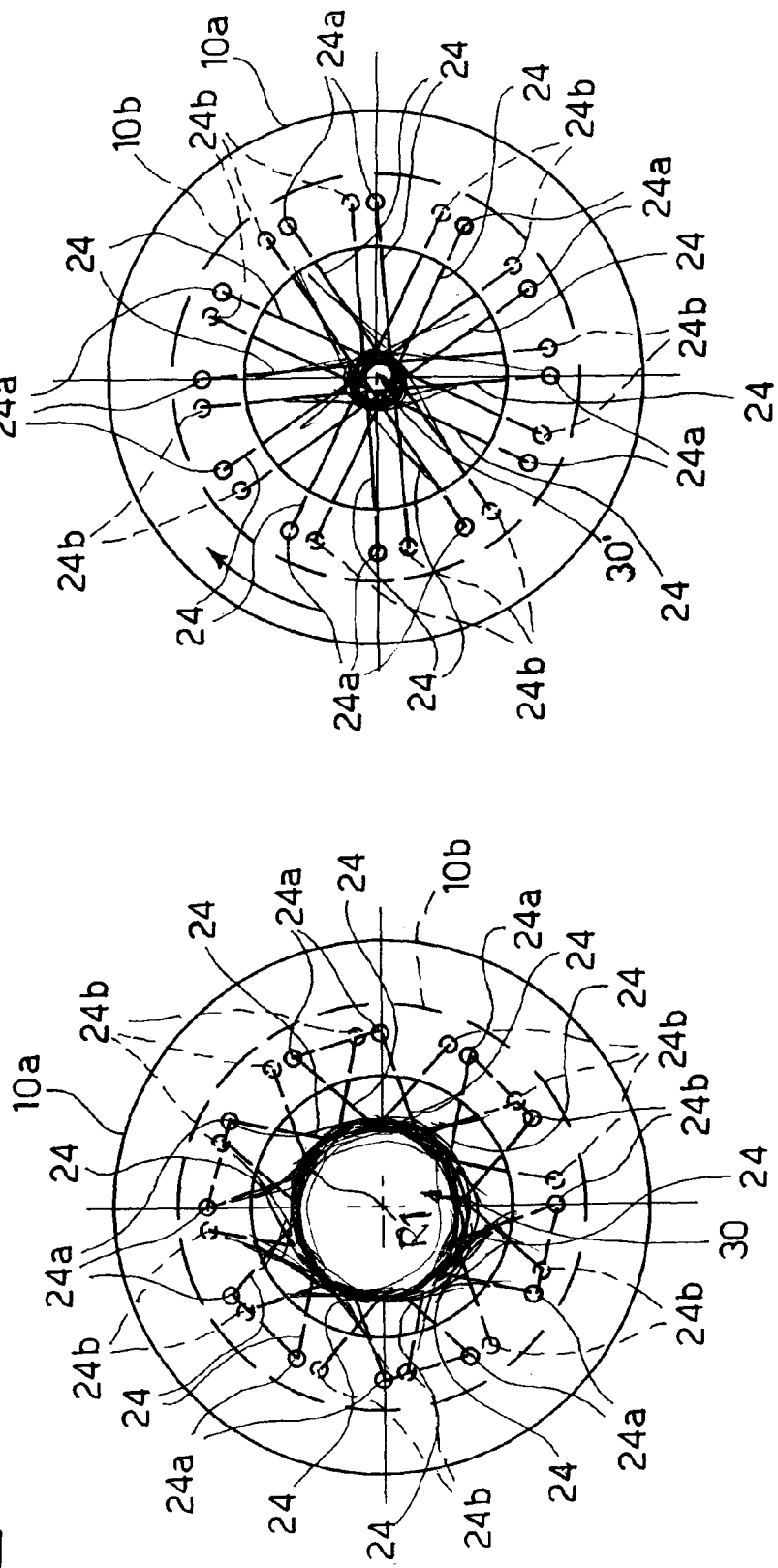
FIGS. 3a and 3b are schematic representations of the operating principle of a device as described herein.

As schematically shown in FIGS. 3a and 3b, operation of the device 10 relies on the relative rotation of the bodies 10a, 10b, which causes displacement of the elements 24 between a first, "outer" position wherein the ends 24a, 24b of each element jointly define a chordal (i.e., off-center) trajectory with respect to the axis X10, and a second, "inner" position wherein, due to the relative rotation movement of the bodies 10a, 10b, the ends 24a, 24b of each element come to define a substantially diametrical trajectory with respect to the axis X10. This substantially diametrical trajectory extends in the vicinity of the axis X10, but does not cross the axis X10. This substantially diametrical trajectory thus corresponds to a trajectory (much) nearer to the axis X10 than the chordal trajectory.

As a result of a movement between the outer, chordal position shown in FIG. 3a and the inner, substantially diametrical position shown in FIG. 3b, the distance between the ends 24a, 24b of each element 24 increases. This increase in length can be accommodated in at least three ways, namely: by using elements 24 that are extendable (e.g., elastic), by allowing either or both ends of the elements 24 to be capable of at least slightly sliding with respect to the bodies 10a, 10b, and/or by having the ends 24a, 24b of the elements remain substantially fixed with respect to the bodies 10a, 10b, with the elements 24 (e.g., in the forms of wire-like bodies) extending loosely between the bodies 10a, 10b in the inner chordal position of FIG. 3a while becoming increasingly taut when approaching the inner substantially diametrical position of FIG. 3b.

The elements 24 comprise an annular array of elements distributed around the axis X10, and the overall result obtainable in passing from the condition illustrated in FIG. 3a to the condition illustrated in FIG. 3b is similar to operation of an obturator in a camera. In other words, in the outer, chordal position of FIG. 3a, the elements 24 jointly define a wider, expanded orifice 30 adapted to receive any of the annular end portions (e.g., the inflow portion R1) of the prosthetic device to be crimped, and in the inner, substantially diametrical position of FIG. 3b, the elements 24 jointly define a narrower orifice 30. In this manner, the annular element (e.g., the inflow portion R1), located within the orifice 30 in the position shown in FIG. 3a, is radially contracted (and thus "crimped") by the joint action of the elements 24 passing from the position of FIG. 3a to the position of FIG. 3b.

As described above, an exemplary embodiment provides for the elements 24 being generally loose when in the outer chordal position of FIG. 3b. The central orifice 30 defined therebetween will thus be a "soft" orifice adapted to resiliently receive the annular element R1 or R2, while allowing for a certain degree of axial displacement with respect to the central axis X10. Also, being generally loose, the elements 24 will accommodate any irregularities of the outer contour of the element R1 or R2, which may be present if, for example, the element 24 is an apertured, mesh-like body. The elements 24 approaching the inner, substantially diametrical position and becoming increasingly taut will thus have the joint effect of crimping the element R1, R2 while increasingly centering the element R1, R2 about the axis X10 by means of an "isostatic" action.

Figure 4:
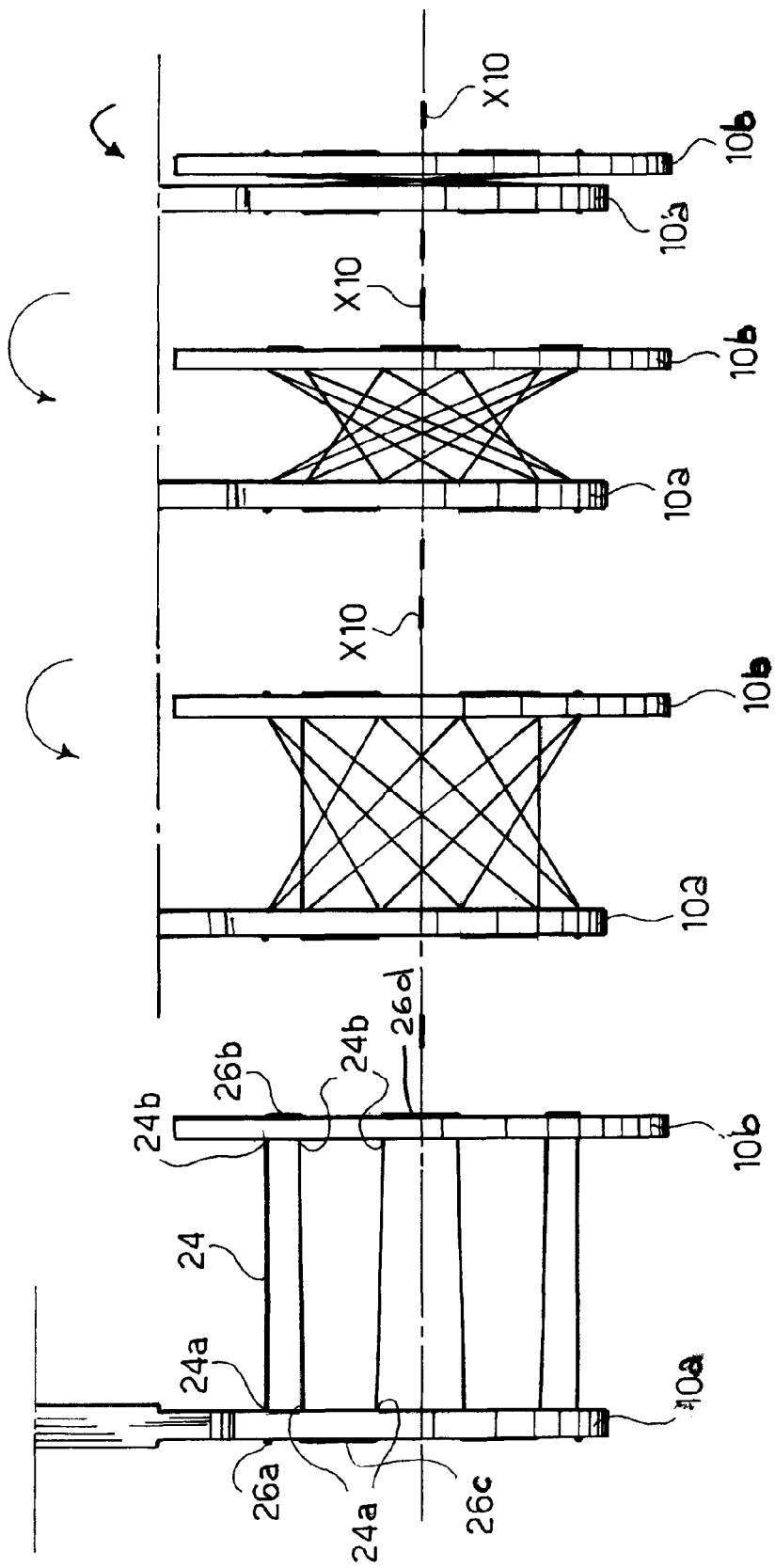
FIGS. 4a-4d show a sequence of steps in assembling a device as described herein.

According to various embodiments, the elements 24 are comprised of subsequent sections of one (or more) wire-like members 26 for example, Dacron™ wire which is threaded in a serpentine pattern between the two bodies 10a, 10b. As shown in FIG. 4a, by way of example, such a serpentine pattern or trajectory of the wire 26 includes, starting from one end 26a of the wire-like element 26 fixed (e.g., by means of a knot or a stitch) to the body 10a, a first portion extending from the body 10a to the body 10b and comprising a first one of the elements 24 having a first end 24a fixed to the body 10a and the opposite end 24b extending through a hole in (and thus linked to) the body 10b, a short portion 26b extending over the surface of the body 10b opposite the body 10a towards another through hole provided in the body 10b, a second portion extending from the body 10b back to the body 10a and comprising a second one of the elements 24 having an end 24b extending through a hole in (and thus linked to) the body 10b and the opposite end 24a extending through a hole in (and thus linked to) the body 10a, another short portion 26c extending over the surface of the body 10a opposite the body 10b towards another through hole provided in the body 10a, a third portion extending again from the body 10a to the body 10b and comprising a third one of the elements 24 having an end 24a extending through a hole in (and thus linked to) the body 10a and the opposite end 24b extending through a hole in (and thus linked to) the body 10b, another short portion 26d extending over the surface of the body 10b opposite the body 10a towards another through hole provided in the body 10b, and so on. This continues until the "other" end (i.e., the end opposite to the 26a) of the wire-like element 26 is fixed to either of the bodies 10a and 10b. While the holes for the wire 26 in the bodies 10a, 10b will typically constitute two circular crown patterns of equally spaced holes, this is not required. Alternatively, these holes may not be equally angularly spaced and/or may be arranged over plural circular trajectories centered around the axis X10.

As shown in FIGS. 4a-4d, once the serpentine pattern of the wire 26 is completed, the two bodies 10a, 10b may be rotated, one with respect to the other, about the common axis X10. This rotational movement first causes the portions of the wire element(s) 26 extending between the two bodies 10a, 10b to become skew with respect to the axis X10 thus notionally defining an hourglass-like geometrical surface substantially similar to a rotation hyperboloid. As shown by the sequence of FIGS. 4a-4d, the "height" of such a hyperboloid (i.e., the distance between the two bodies 10a, 10b) gradually decreases as the rotation movement advances.

When the two bodies 10a, 10b are placed one against each other as shown in FIG. 4d, with the wire-like element 26 lying therebetween, the elements 24 are arranged as depicted in FIG. 3a (i.e., the elements 24 define a wider, expanded orifice 30). Of course, the sequence depicted in FIGS. 4a-4d is just one exemplary way of obtaining an "obturator-like" arrangement of the elements 24. The arrangement described herein allows the device 10 to be relatively simple and inexpensive. It also allows the device 10 to be a disposable implement for one-time use in the operational theatre to crimp an implantable device.

The brake member 20 is configured to stop the crimping action at any desired position, including intermediate positions. This feature may be useful, for instance, in the multiple crimping arrangement illustrated in FIG. 1. First, the operator can crimp a first of annular end portions (e.g., the inflow portion R1). Then, with the inflow portion R1 crimped and safely retained within the device 10 and secured by the respective brake member 20, the operator can crimp the opposite outflow portion R2, using the twin devices 101 and 102. The sequence of operations may also be reversed, such that the outflow portion R2 is crimped before the inflow portion R1. FIG. 1 shows an exemplary situation wherein the inflow end portion R1 has been crimped using the device 10, and the outflow end portion R2 is in the process of being crimped by using the twin devices 101 and 102. This occurs while the device 10 is "locked" by the brake member 20. The operator is thus in a position to fully concentrate on the crimping operation of the outflow portion R2.

Figure 5:
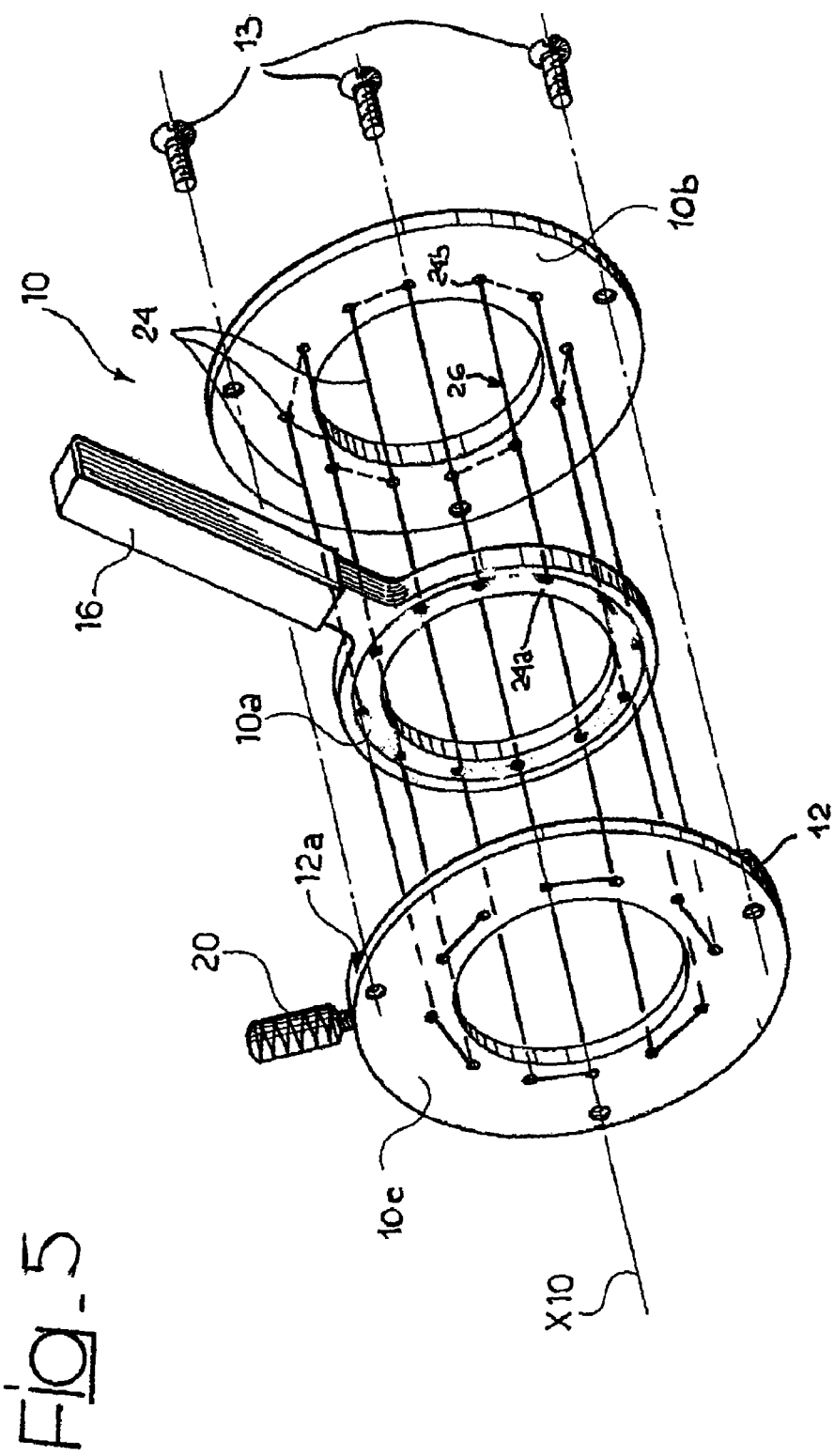
FIGS. 5 and 6 show an alternative embodiment of a crimping device as described herein.

FIG. 5 shows an alternative embodiment where the "twin" devices 101, 102 are incorporated to a single, integrated structure. Direct comparison of FIG. 5 to FIG. 2 shows that the integrated structure of FIG. 5 again includes the annular bodies 10a, 10b, 10c, with the body 10a interposed between the bodies 10b, 10c and capable of relative movement with respect to the bodies 10b, 10c. The body 10a can thus be rotated with respect to the bodies 10b and 10c (which are fixed to each other via the screws 13), as a result of actuation of the lever 16. While the embodiment of FIG. 2 includes a body 10c that is unperforated (except for the holes provided for the screws 13), in the embodiment of FIG. 5, the body 10c includes a "crown" of holes essentially similar to that provided in the body 10b.

In the embodiment of FIG. 5, the wire 26 is again imparted a serpentine pattern or trajectory starting, for example, from one end fixed to the body 10b and including: a first portion extending from the body 10b through a hole in the body 10a up to the body 10c, a short portion extending over the surface of the body 10c opposite the body 10a towards another through hole provided in the body 10c, a second portion extending from the body 10c through a hole in the body 10a back to the body 10b, another short portion extending over the surface of the body 10b opposite the body 10a towards another through hole provided in the body 10b, a third portion extending again from the body 10b through a hole in the body 10a up to the body 10c, another short portion extending over the surface of the body 10c opposite the body 10a towards another through hole provided in the body 10b, and so on. This continues until the "other" end of the wire-like element 26 is fixed to any of the bodies 10a, 10b or 10c.

Figure 6:
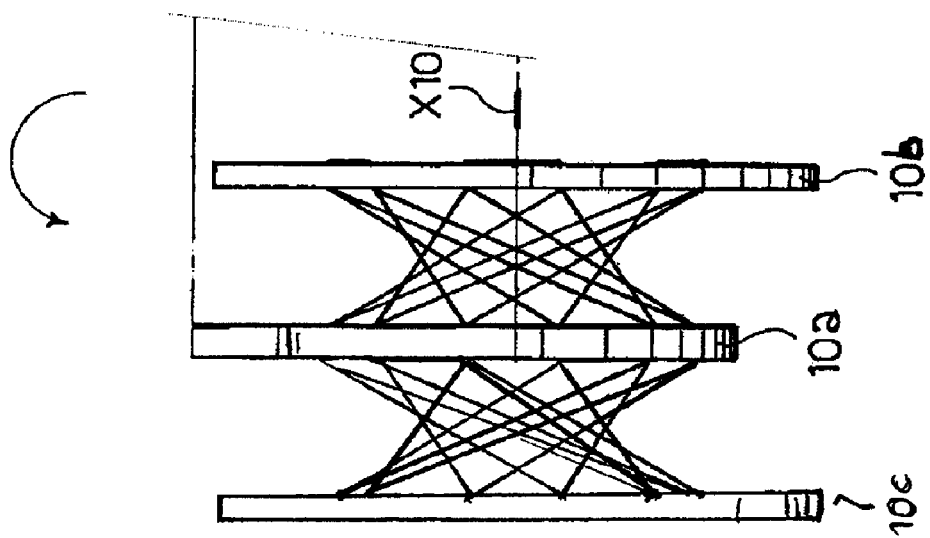

As schematically shown in FIG. 6 (which generally corresponds to FIG. 4c), once the serpentine pattern of the wire 26 is completed, the body 10a can be rotated with respect to the bodies 10b, and 10c about the common axis X10. As shown, this rotational movement first causes the portions of the wire element(s) 26 extending on either side of the body 10a towards the two bodies 10b and 10c to become skew with respect to the axis X10 thus notionally defining on either side of the body 10a hourglass-like geometrical surfaces substantially similar to a rotation hyperboloid. The "height" of such hyperboloids (i.e. the distance between the body 10a and either of the bodies 10b, 10c) gradually decreases as the rotation movement advances.

When the two bodies 10b, 10c are placed against the body 10a with the wire-like element 26 lying therebetween, the elements 24 are positioned on both sides of the body 10a in an "obturator-like" arrangement or array as shown in FIG. 3a. These arrays of elements 24 are arranged side-by-side (e.g., at an axial distance of a few millimeters or less) and can thus jointly co-operate in crimping, for example, the outflow portion R2 of a valve as schematically shown in FIG. 1. These two "twin" arrays of elements 24 arranged side-by-side can be operated by acting on the (single) lever 16 of the body 10a and can be locked at any desired crimping position under the action of the brake member 20, which can be selectively operated (e.g., tightened or loosened) to prevent or permit rotation of the body 10a with respect to the bodies 10b and 10c.

Regardless of the embodiment selected, the wire-like characteristic of the elements 24 may be advantageous, as these wire-like elements may easily adapt to an irregular (e.g., V-shaped) outer surface of the device/part to be crimped. Additionally, the wire-like characteristic of the elements 24 may be advantageous in that these elements do not prevent penetration of a sheath-like or cap-like element possibly slid over the crimped device or part to constrain it in the crimped position.

As an alternative to the wire-like configuration, alternative embodiments may include elements 24 in the form of blade-like elements of members (which may be flexible) possibly extending along helical trajectories between the two bodies 10a, 10b. These blade-like elements may be advantageous in more extensively countering any tendency of the device/part being crimped to becoming undesirably kinked during crimping. Also, while in the exemplary embodiments described and shown herein, the bodies 10a, 10b, and 10c are in the form of closed annular bodies, any of them can take the form of an open body (e.g., a sort of "split" ring). By way of example, a flexible element or member can be a wire-like member, a wire, a string, a thread made of natural or synthetic materials, a plastic, a metal, and the like.

In yet another variant of the invention, a device for crimping a heart valve prosthesis onto a delivery system is also provided. Such a device may include multiple crimping modules as shown in FIG. 1. Each respective one of the crimping modules is located in a distinct crimping plane one from another. It is appreciated that one crimping module (e.g., 10) can act on the inflow portion of the device, while a second crimping module (e.g. 101, 102) can act, simultaneously or at a different point in time, on the outflow portion of the device. Similarly, each of the modules can be mechanically connected (as shown e.g. in FIGS. 5 and 6) so that a first module acts on a first portion of the device, while at a predetermined moment in time the other one or more modules act on another portion of the device. By way of further example, three, four, five or more crimping modules act on different portions of the device to crimp it on different sections of the delivery system. In another variant, the crimping planes lie parallel to each other (e.g., in a stacked arrangement). In another variant, the crimping planes intersect or lie in a non-parallel relationship to each other.

Consequently, without prejudice to the underlying principles of the invention, details and embodiments may vary, even significantly, with respect to what has been described and illustrated by way of example only, without departing from the scope of the invention as defined by the annexed claims. Likewise, various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A device for crimping an expandable prosthetic heart valve, the device comprising:
   a first annular body and a second annular body arranged for relative rotation generally about an axis; and
   an array of linear crimping elements having first ends coupled to the first annular body and second ends coupled to the second annular body, wherein the array of linear crimping elements defines an orifice;
   wherein the first body and the second body are configured to rotate about the axis between a first position, wherein the crimping elements define the orifice with a first diameter and a second position, wherein the crimping elements define the orifice with a second diameter;
   wherein the crimping elements include a plurality of flexible elements extending in a generally serpentine pattern between the first and second annular bodies, wherein the pattern includes portions of the flexible elements extending between the first and the second annular bodies to define the crimping elements.

2. The device of claim 1 further including a brake member selectively actuatable to prevent the relative rotation of the first and second annular bodies.

3. The device of claim 1, wherein the flexible elements are elastic to allow for the variation of the distance of the respective opposite ends of the crimping elements in the first and the second positions.

4. The device of claim 1, wherein the flexible elements are substantially unextendable elements, whereby the crimping elements are generally loose in the first position and become increasingly taut as the first and second annular bodies move towards the second position.

5. The device of claim 1 further including a peripheral rim fixed to the second annular body and extending around the first annular body, such that the first and the second annular bodies are generally centered about the axis.

6. The device of claim 5 further including:
   a third annular body, wherein the first annular body is interposed between the second and the third annular bodies, the first annular body adapted for relative rotation with respect to the second and the third annular bodies, and
   a second array of linear crimping elements provided between the first annular body and either of the second or third annular bodies.

7. The device of claim 6 further including at least one flexible member extending in a generally serpentine pattern, wherein the pattern includes portions of the flexible member extending between the second and the third annular bodies through the first annular body to define the arrays of linear crimping elements.

8. The device of claim 1 further comprising a prosthetic heart valve having an end portion generally disposed within the orifice.

9. A device for crimping an expandable prosthetic heart valve, the device comprising:
   a first annular body, a second annular body, and a third annular body each arranged generally about an axis, the first annular body interposed between the second annular body and the third annular body, the second annular body including a peripheral rim extending around the first annular body, such that the first and the second annular bodies are generally centered about the axis;
   wherein the first annular body is arranged for relative rotation with respect to each of the second annular body and the third annular body;
   an array of linear crimping elements having first ends coupled to the first annular body and second ends coupled to the second annular body, wherein the array of linear crimping elements defines an orifice; and
   a second array of linear crimping elements provided between the first annular body and the third annular body;
   wherein the first body and the second body are configured to rotate about the axis between a first position, wherein the crimping elements define the orifice with a first diameter and a second position, wherein the crimping elements define the orifice with a second diameter;
   wherein the crimping elements include a plurality of flexible elements extending in a generally serpentine pattern between the first and second annular bodies, wherein the pattern includes portions of the flexible elements extending between the first and the second annular bodies to define the crimping elements.

10. The device of claim 9 further including at least one flexible member extending in a generally serpentine pattern, wherein the pattern includes portions of the flexible member extending between the second and the third annular bodies through the first annular body to define the arrays of linear crimping elements.

* * * * *